(12) United States Patent
Prytkov

(10) Patent No.: US 9,104,900 B2
(45) Date of Patent: Aug. 11, 2015

(54) RIDGE PATTERN RECORDING SYSTEM

(71) Applicant: Abilma LLC, St. Petersburg (RU)

(72) Inventor: Anton S. Prytkov, St. Petersburg (RU)

(73) Assignee: ABILMA LLC, St. Petersburg (RU)

(*) Notice: Subject to any disclaimer, the term of this patent is extended or adjusted under 35 U.S.C. 154(b) by 23 days.

(21) Appl. No.: 14/175,350

(22) Filed: Feb. 7, 2014

(65) Prior Publication Data
US 2014/0153792 A1 Jun. 5, 2014

Related U.S. Application Data

(63) Continuation of application No. PCT/RU2012/000672, filed on Apr. 8, 2012.

(30) Foreign Application Priority Data

Aug. 10, 2011 (RU) .............................. 2011134823

(51) Int. Cl.
G06K 9/00 (2006.01)
A61B 5/117 (2006.01)
G06K 9/20 (2006.01)

(52) U.S. Cl.
CPC ............ *G06K 9/0008* (2013.01); *A61B 5/1172* (2013.01); *G06K 9/00013* (2013.01); *G06K 9/00046* (2013.01); *G06K 9/2018* (2013.01)

(58) Field of Classification Search
CPC ... G06K 9/0008; G06K 9/0093; G06K 9/001; G06K 9/0067; G06K 9/0073; G06K 9/4647
See application file for complete search history.

(56) References Cited

U.S. PATENT DOCUMENTS

| 5,230,025 | A | 7/1993 | Fishbine et al. |
| 5,859,420 | A | 1/1999 | Borza |
| 6,928,195 | B2 | 8/2005 | Scott et al. |
| 8,520,911 | B2* | 8/2013 | Fenrich et al. ............... 382/124 |
| 2004/0208346 | A1* | 10/2004 | Baharav et al. ............... 382/124 |

FOREIGN PATENT DOCUMENTS

| RU | 2051415 C1 | 12/1995 |
| RU | 2320261 C2 | 3/2008 |

* cited by examiner

Primary Examiner — Stephen R Koziol
Assistant Examiner — Totam Le
(74) Attorney, Agent, or Firm — Arent Fox LLP; Michael Fainberg

(57) ABSTRACT

Disclose a system for recording ridge patterns comprising a light source, a component which determines the position of a scanning surface, an optical system, a multi-element image sensor, an electronic memory and a processing device, wherein the output electronic image from the system is linked by means of merging in the processing device to at least two intermediate images which are linked to the optical image from the scanning surface.

5 Claims, 3 Drawing Sheets a b

RIDGE PATTERN RECORDING SYSTEM

CROSS-REFERENCE TO RELATED APPLICATION

This application is a continuation of International Application No. PCT/RU2012/000672, filed Aug. 8, 2012, which claim benefit of priority to Russian Application 2011134823, filed Aug. 10, 2011.

TECHNICAL FIELD

The invention relates generally to the field of biometrics, and particularly to systems for the automatic recording of ridge patterns.

BACKGROUND

FIG. 1 shows a diagram of a typical system for recording ridge patterns. A source of light 1 radiates onto a component 2 which determines the position of the scanning surface 3 for the subject to be recorded, such as the ridge lines on the finger or the palm of the hand. On the scanning surface, the luminous flux from the source of light ends up carrying an image of this ridge pattern on the basis of the differences in the reflection of areas corresponding to the troughs and peaks of the ridge pattern. The optical system, as a rule including a collecting lens 4, a system of mirrors 5, an objective lens 6, protective glass 7 and microlenses 8 over the image sensor, takes this flux and creates an image of the ridge pattern on the light-sensitive surface 9 of a multi-element image sensor. The image sensor converts the image from an optical image into an electronic digital image in the form of an array of intensity values proportional to the radiant flux incident on the corresponding light-sensitive element, and transmits this image to the electronic memory 10. The processing unit 11 standardizes the scale of this electronic image, thus creating the output image of the system.

The component which determines the position of the subject to be recorded is, as a rule, designed as an optically transparent isosceles rectangular prism. However, there are variants in the design of the system for recording ridge patterns in which prisms of complex form, cylindrical components or plane-parallel plates act as the component determining the position of the scanning surface. In rarer variants, the body element of the system is the component determining the position of the scanning surface.

The number of mirrors in the optical system may vary and determines the shape and overall dimensions of the system.

The radiation sensor, as a rule, is constructed as a bar or matrix of metal oxide semiconductor transistors or charge-coupled devices.

One general disadvantage of said systems, as a consequence of very strict requirements on the quality of the image, is the necessity of using image sensors with relatively large light-sensitive elements, which leads to a considerable overall area of the sensor working surface and, as a consequence, to an extremely high cost of systems constructed with their use.

The considerable price of large-area sensors is due to the high cost of the silicon wafers from which they are manufactured and the low useful yield percentage of these wafers.

Thus, FIG. 2a shows the arrangement on the 150 mm diameter silicon wafer 12 of crystals 13 for a typical image sensor for a system for recording the ridge pattern of the palm of the hand with a distribution of 1000 dpi. A sensor of this kind has dimensions for its light-sensitive elements of 6.8 micrometers and contains 7216 elements along the horizontal and 5412 along the vertical. It may be seen from the figure that only four crystals of this nature may be accommodated on the wafer. Moreover; in this case, the useful area of the wafer usable for the manufacture of crystals accounts for around 50% of its total area. If a total of four critical production faults 14 are permitted during manufacture, but these are arranged as shown in FIG. 2a, for example, then not one serviceable crystal will be obtained from the wafer.

If a sensor is built with the same number of light-sensitive elements, but 1.4 micrometers in size, then the arrangement of the crystals on the 150 mm diameter wafer 15 may be, for example, as illustrated in FIG. 2b. In this case, the wafer accommodates 137 crystals 16 which occupy as much as 80% of the area of the wafer. At the same time, if a total of four critical production faults 17 are permitted during manufacture, arranged as shown in FIG. 2a, then 133 serviceable crystals will be obtained from the wafer. The losses due to defects thereby amount to just 3% of the total number of crystals on the wafer.

However, notwithstanding the obvious advantages, the use in systems for recording ridge patterns of sensors with small light-sensitive elements is constrained by the quality of the image formed, which is inadequate for compliance with current standards in the field of biometrics, particularly by noise and diffusion of the charge between the elements. FBI EBTS Appendix F is currently a key standard for ridge pattern recording systems.

There are a few variants for the design of systems for recording ridge patterns which bring about the required resolution and size of the scanning field whilst using relatively cheap image sensors.

Thus, U.S. Pat. No. 5,859,420, dated Dec. 1, 1999, classified under IPC G01B11/124, discloses a system in which the resolution of the system for recording ridge patterns is increased by subdividing the systems into a plurality of channels, each of which forms a separate part of the image of the subject to be recorded, after which the parts of the image are combined into the output image.

U.S. Pat. No. 6,928,195, dated Sep. 8, 2005, classified under IPC G06K9/32, discloses a system allowing an increase in the resolution of a system for recording ridge patterns without increasing the number of light-sensitive elements in the image sensor, by using a nutating mirror in the system to create a plurality of displaced intermediate images and forming an output image in which the elements of the intermediate images are interlaced.

This system is the closest analogue to the proposed invention. Its chief drawback is the presence of further elements and procedures which, although permitting the use of a relatively inexpensive sensor, do themselves make an additional contribution to the expense of the system and lower its reliability. As a consequence, a substantial reduction in the total cost of the system is not achieved, while at the same time reliability is reduced, the overall size is increased, the energy consumption is greater and the operating speed of the system is slower.

SUMMARY

The object of the present invention is to provide a system for recording ridge patterns having a low cost and high reliability and at the same time providing high-quality images, small overall dimensions, a high operating speed and reduced energy consumption.

Said object is achieved in that the system for recording ridge patterns includes a source of light, an element determining the position of the scanning surface, an optical system, a multi-element image sensor, an electronic memory for storing images and a processing unit, wherein the output image from the system is electrically linked in the electronic memory with at least two intermediate images, by blending in the processing unit the intensity values of elements of the intermediate images corresponding to different intermediate images of one and the same region on the scanning surface, and assigning the value obtained for the intensity corresponding to this region to an element of the output image, and each of the intermediate images is linked electrically with light-sensitive elements of the image sensor, which are linked optically with the light source and the ridge pattern scanning surface by way of the image of the ridge pattern scanning surface formed by the optical system, wherein, in the spectral range of sensitivity of the image sensor, the total flux of useful light with wavelengths less than the boundary wavelength L is at least five times greater than the total flux of stray light with wavelengths greater than L, and the value of L satisfies the condition:

$$\frac{0.37\ L^{1.5}}{A \cdot N \cdot T^{1.2}} < 1,$$

where L is the boundary wavelength, expressed in micrometers;
T is the interval between centres of the elements sensitive to the useful light in the image sensor, expressed in micrometers;
A is the effective numerical aperture of the optical system forming the image of the scanning surface on the light-sensitive surface of the image sensor, on the image sensor side;
N is the number of light-sensitive elements in the image sensor per one element of the output image.

In one example embodiment, a computer may be employed as the image processing unit for merging intermediate images.

In another example embodiment, a digital signalling processor may be employed as the image processing unit for merging intermediate images.

In another example embodiment, the processing unit, electronic memory and image sensor may be integrated into a single structural element.

Yet in another example embodiment, the image sensor may be monochromatic.

The technical result provided by the set of features listed is a reduction in cost, an increase in reliability, the provision of high image quality, small overall dimensions, a high operating speed and reduced energy consumption of the system for recording ridge patterns.

BRIEF DESCRIPTION OF THE DRAWINGS

FIGS. 2a and 2b show the arrangement of crystals in the image sensor with 7216 light-sensitive elements along the horizontal and 5412 along the vertical on a 150 mm diameter wafer with differing dimensions of the light-sensitive elements, in which FIG. 2a shows the crystals with 6.8 micrometer elements, and FIG. 2b shows the crystals with 1.4 micrometer elements.

DETAILED DESCRIPTION

Figure 1:
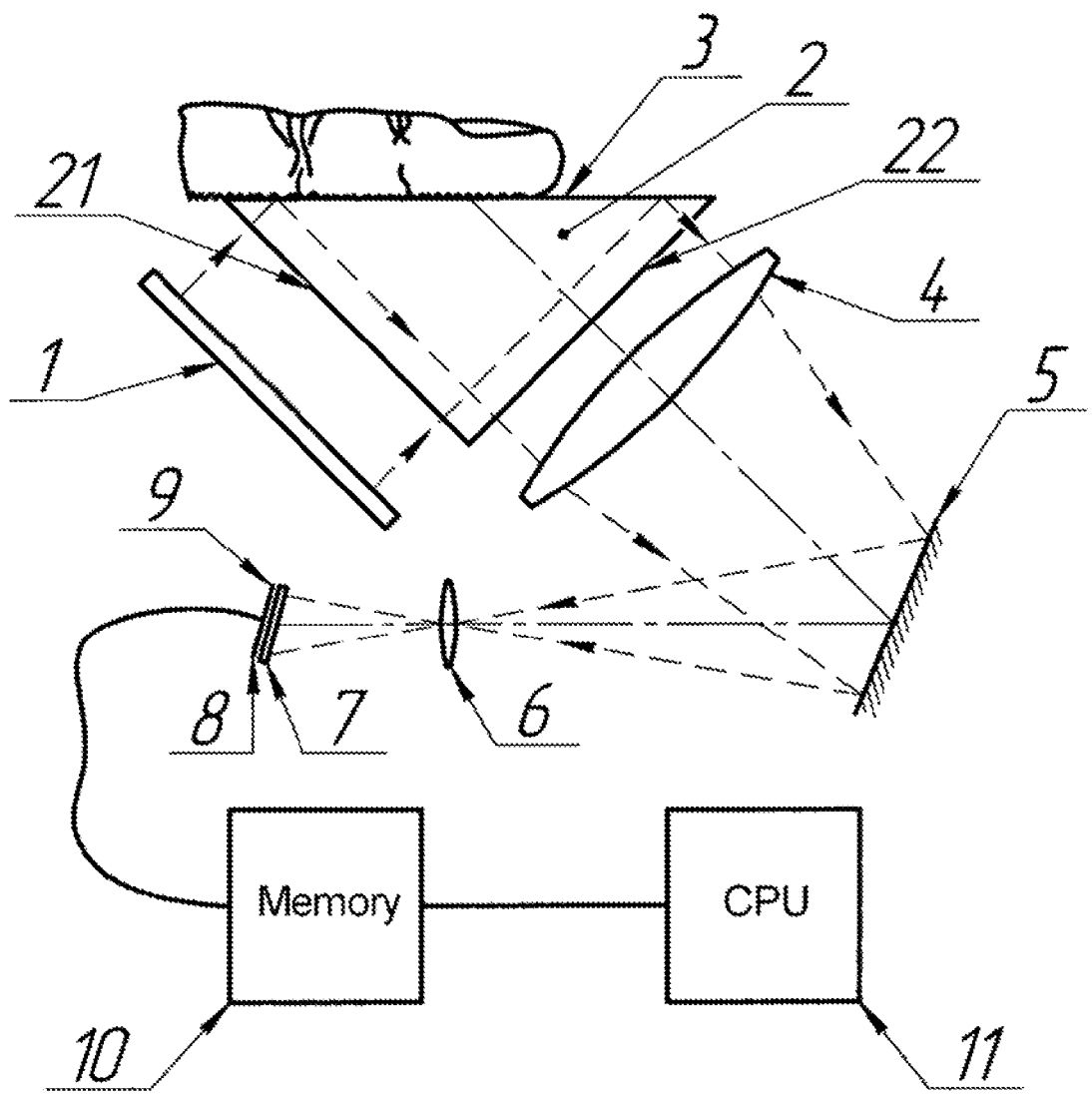
FIG. 1 is a typical schematic diagram of the design of a ridge pattern recording system.
Figure 2:
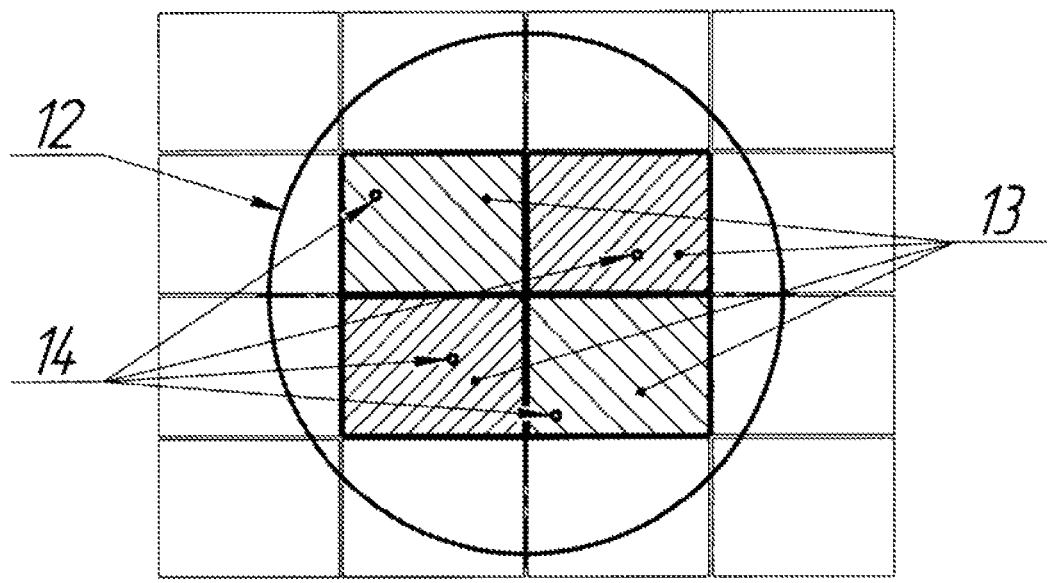
Figure 2:
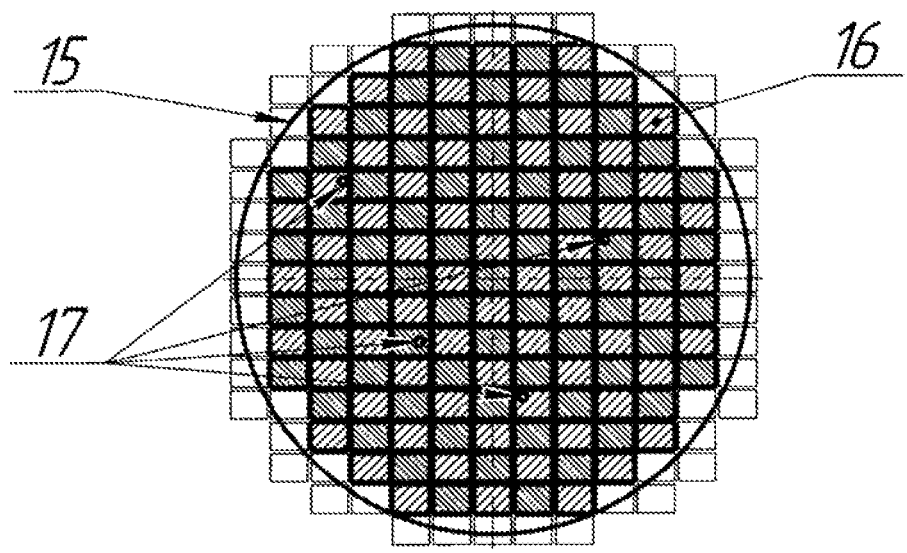
Figure 3:
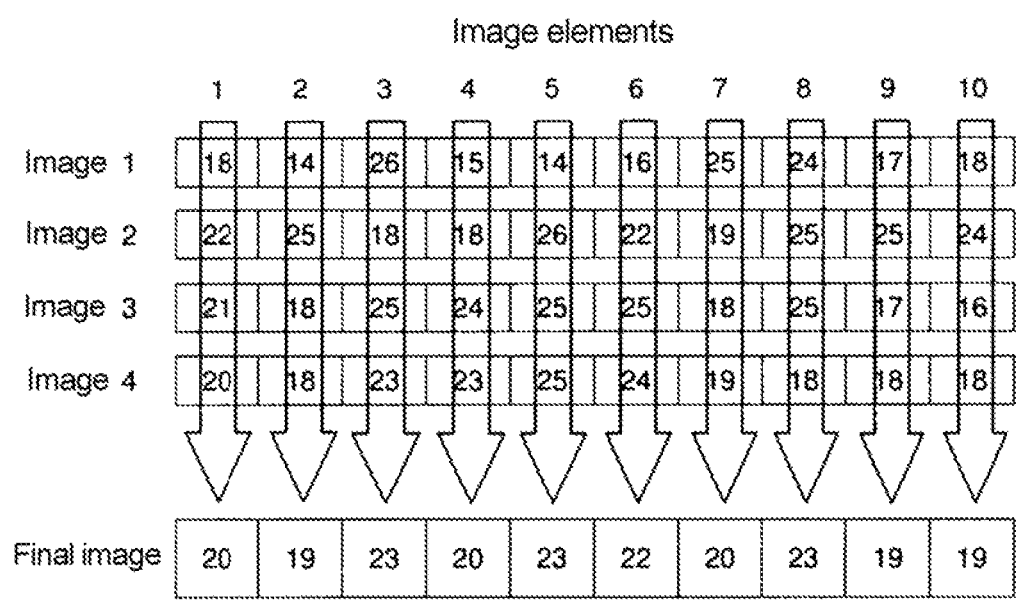
FIG. 3 is a schematic diagram of merging the intermediate images into output image by averaging the intensity values for the elements of the images.

An example embodiment of the invention may be seen in the diagram shown in FIG. 1. A source of light, taking the form of a light panel 1, constructed as light-emitting diodes with a dominant radiation wavelength of 470 nanometers, shines on an isosceles rectangular prism 2 made from optically transparent material. Passing through the input leg face of the prism 21, the light is incident at an angle of total internal reflection on the hypotenuse face 3, itself determining the ridge pattern scanning surface. The subject to be recorded, such as the fingerprint or the palm of the hand, is placed on this surface. At the points corresponding to the peaks of the ridge pattern, the luminous flux from the light source is partially absorbed by the object to be recorded; in the remaining areas it is fully reflected by the hypotenuse face of the prism. In this way the luminous flux ends up carrying an image of the ridge pattern to be recorded. The light subsequently passes through the exit leg face 22 of the prism and the collecting lens 4, is reflected on the mirror 5 and is incident on objective lens 6. An interference coating is applied to the working surface of one of the optical components in the objective lens to act as a clipping light filter blocking radiation with a wavelength over 490 nanometers. The objective lens, with an exit numerical aperture of at least 0.08, forms an image of the subject to be recorded on the light-sensitive surface 9 of the monochrome camera constructed as a matrix of transistors in a metal oxide semiconductor with spacings between elements of 1.7 micrometers, wherein one light-sensitive element is needed for one element of the required resolution on the object to be recorded, and the elements in the optical system and image sensor are rigidly fastened to form a single body. The camera creates a digital image of the object to be recorded in the form of an array of intensity values associated with the luminous flux incident on the corresponding light-sensitive element and transmits this through a USB interface to the memory 10 of the computer with the processor 11. Four intermediate images, from which one output image is formed, are thus transmitted. To achieve this, the program calculates an average intensity value for the same element over all four intermediate images and assigns the value obtained to the corresponding element in the output image. The principle of this merging for portions of the image is shown graphically in FIG. 3.

In another example design of the system, the program merges the images by temporarily averaging and resealing the intensity values, transforming the range of intensity from 0 to 255 units to a range from 0 to 65535. This sums the merged intensity values, multiplies the value obtained by the specified coefficient and assigns the value obtained to the corresponding element of the output image.

In yet another example embodiment of the invention, to simplify the procedure for adjusting the system, and precisely to correct the need for manual regulation of the optical magnification, the objective lens forms the image covering a number of light-sensitive elements exceeding the required number of elements in the output image. At the same time the software modifies the scale, by compression, of the output image. Thus, for example, if the objective lens forms the image while covering, in each of two perpendicular directions, a number of light-sensitive elements 10% greater than is required by the elements in the corresponding directions in the output image, the software compresses the data, each element being assigned $1.1^2=1.21$ light-sensitive elements of the sensor in the output image. Moreover, along with the simplification of adjustment, in this case in accordance with said condition $0.37 \cdot L1.5/(A \cdot N \cdot T1.2) < 1$, it becomes possible to use a wider spectral range and thereby to provide a greater radiant flux, without detriment to the quality of the image and without increasing energy consumption.

The applicant has manufactured several specimen palm ridge pattern scanners with a scanner surface size of 129×129 mm and with a resolution on this surface equivalent to 500 dots per inch, including specimens with the parameters specified above. A device with said parameters was the first known ridge pattern scanner having such a small size of light-sensitive elements which has been able to produce an image quality complying with the FBI EBTS Appendix F standard, which is available from www.fbibiospecs.org/ebts.html. Experimental data confirmed that with the merging of the number of intermediate images required for the present sensor and with implementation of said ratio 0.37 L1.5/(A·N·T1.2)<1 it is possible to construct a ridge pattern recording system complying with said standard using any available image scanner with small light-sensitive elements. At the same time, the fact that the working radiant flux is at least five times greater than the parasitic radiant flux means that this parasitic flux has an influence on the quality of the image at a level equivalent to the influence of secondary factors such as the scattering of light and parasitic reflections in the optical system.

As a consequence of the small size of the light-sensitive elements and the use of a monochromatic camera, each element of which is sensitive to the working radiation, the total size of the sensor area in the image sensor used is comparatively small, leading to a reduction in the cost of the sensor and to a lower energy consumption. Also because of the small size of the light-sensitive surface, the focal length of the objective lens is significantly shorter than in the closest analogue, leading to a reduction in the overall dimensions of the system and the cost of the lens. There are no moving elements in the system, leading to an increase in the operating speed and reliability of the system by comparison with its nearest analogue. Merging the intermediate images and using radiation with relatively short wave lengths has allowed the capture of a high-quality image, complying with the FBI EBTS Appendix F standard.

The invention claimed is:

1. A system for recording ridge patterns, the system comprising:
  a light source configured to emit light;
  an element having a scanning surface configured to reflect light based on positions of the ridge patterns on the scanning surface;
  an optical system configured to form at least one image of the scanning surface based on the reflected light;
  an image sensor with a plurality of light-sensitive elements, the image sensor configured to generate a plurality of intermediate images based on the at least one image formed by the optical system;
  an electronic memory configured to store the plurality of intermediate images; and
  a processing unit configured to generate an output image by averaging intensity values of respective elements of the plurality of intermediate images corresponding to a same region of the scanning surface and assign the average intensity value to a corresponding element of the output image,
    wherein each of the plurality of intermediate images is linked electrically with the plurality of light-sensitive elements of the image sensor, and the plurality of light-sensitive elements are linked optically with the light source and the scanning surface,
    wherein, in a spectral range of sensitivity of the image sensor, a total flux of useful light with wavelengths less than a boundary wavelength L is at least five times greater than a total flux of stray light with wavelengths greater than the boundary wavelength L, and L satisfies the condition:

$$\frac{0.37\ L^{1.5}}{A \cdot N \cdot T^{1.2}} < 1$$

wherein L is the boundary wavelength of the light emitted from the light source, expressed in micrometers,
T is an interval between centres of the plurality of light sensitive elements of the image sensor, expressed in micrometers,
A is a numerical aperture of the optical system configured to form the at least one image of the scanning surface on the image sensor, and
N is a number of light-sensitive elements in the image sensor per one element of the output image.

2. The system of claim 1, wherein the processing unit is a computer.

3. The system of claim 1, wherein the processing unit is a digital signal processor.

4. The system of claim 1, wherein the image sensor, the electronic memory and the processing unit are integrated into a single structural element.

5. The system of claim 1, wherein the image sensor is monochromatic.

* * * * *